(12) United States Patent
Eckhardt et al.

(10) Patent No.: US 8,623,189 B2
(45) Date of Patent: Jan. 7, 2014

(54) ELECTROCHEMICAL GAS SENSOR WITH AN IONIC LIQUID ELECTROLYTE SYSTEM INCLUDING AT LEAST ONE MONOALKYLAMMONIUM, DIALKYLAMMONIUM, OR TRIALKYLAMMONIUM CATION

(75) Inventors: Rolf Eckhardt, Alzenau (DE); Ralf Warratz, Bonn (DE)

(73) Assignee: MSA Auer GmbH, Berlin (DE)

( * ) Notice: Subject to any disclaimer, the term of this patent is extended or adjusted under 35 U.S.C. 154(b) by 205 days.

(21) Appl. No.: 13/131,391

(22) PCT Filed: Nov. 25, 2009

(86) PCT No.: PCT/EP2009/065819
§ 371 (c)(1),
(2), (4) Date: Jul. 6, 2011

(87) PCT Pub. No.: WO2010/063626
PCT Pub. Date: Jun. 10, 2010

(65) Prior Publication Data
US 2011/0253534 A1 Oct. 20, 2011

(30) Foreign Application Priority Data

Dec. 1, 2008 (DE) .......................... 10 2008 044 240

(51) Int. Cl.
*G01N 27/413* (2006.01)
(52) U.S. Cl.
USPC .......................................... 204/431; 73/23.2
(58) Field of Classification Search
USPC ...................... 73/19.01–31.07; 204/410, 411, 204/421–429; 205/781, 783.5–785, 787
See application file for complete search history.

(56) References Cited

U.S. PATENT DOCUMENTS

| 3,328,277 A | 6/1967 | Solomons et al. |
| 4,169,779 A | 10/1979 | Tataria et al. |
| 4,474,648 A | 10/1984 | Tantram et al. |
| 5,228,974 A | 7/1993 | Kiesele et al. |
| 5,318,912 A | 6/1994 | Silver et al. |
| 5,565,075 A | 10/1996 | Davis et al. |

(Continued)

FOREIGN PATENT DOCUMENTS

| CN | 1767242 A | 5/2006 |
| CN | 1989405 A | 6/2007 |

(Continued)

OTHER PUBLICATIONS

A.I. Bhatt, et al., "A critical assessment of electrochemistry in a distillable room temperature ionic liquid, DIMCARB", Green Chemistry, vol. 8, 2006, p. 161-171.*

(Continued)

*Primary Examiner* — J. Christopher Ball
(74) *Attorney, Agent, or Firm* — The Webb Law Firm

(57) ABSTRACT

An electrochemical gas sensor includes an ionic liquid as electrolyte. The ionic liquid includes at least one cation selected from the group of a monoalkylammonium cation, a dialkylammonium cation, and a trialkylammonium cation. The individual alkyl groups of the cation can be branched or unbranched and have 1 to 4 carbon atoms. The individual alkyl groups of the cation can be the same or different in case of the dialkylammonium cation and the trialkylammonium cation. In a number of embodiments, the individual alkyl groups have 2 to 4 carbon atoms.

20 Claims, 6 Drawing Sheets

(56) References Cited

U.S. PATENT DOCUMENTS

| | | |
|---|---|---|
| 5,667,653 A | 9/1997 | Schneider et al. |
| 5,855,809 A | 1/1999 | Angell et al. |
| 5,914,019 A | 6/1999 | Dodgson et al. |
| 7,060,169 B2 | 6/2006 | Röhrl |
| 7,147,761 B2 | 12/2006 | Davis et al. |
| 7,381,314 B2 | 6/2008 | Inoue et al. |
| 7,591,964 B2 | 9/2009 | Ivanov et al. |
| 7,758,735 B2 | 7/2010 | Hengstenberg et al. |
| 2004/0033414 A1 | 2/2004 | Rohrl |
| 2004/0133116 A1 | 7/2004 | Abraham-Fuchs et al. |
| 2005/0045493 A1 | 3/2005 | Mahurin et al. |
| 2006/0021873 A1 | 2/2006 | Mett |
| 2006/0278536 A1 | 12/2006 | Burrell et al. |
| 2007/0026295 A1 | 2/2007 | Angell et al. |
| 2007/0185330 A1 | 8/2007 | Walker |

FOREIGN PATENT DOCUMENTS

| | | |
|---|---|---|
| DE | 4238337 C2 | 6/1994 |
| DE | 69017039 T2 | 7/1995 |
| DE | 102004037312 A1 | 3/2006 |
| DE | 102005020719 B3 | 9/2006 |
| EP | 1384069 B1 | 6/2006 |
| GB | 2395564 A | 5/2004 |
| GB | 2426343 A | 11/2006 |
| JP | 2003172723 A | 6/2003 |
| JP | 2005524825 A | 8/2005 |
| JP | 200690991 A | 4/2006 |
| JP | 200698269 A | 4/2006 |
| JP | 200864578 A | 3/2008 |
| RU | 2147120 C1 | 3/2000 |
| WO | 03098205 A1 | 11/2003 |
| WO | WO 2007/115801 A1 * | 10/2007 |
| WO | 2008110830 A1 | 9/2008 |

OTHER PUBLICATIONS

H. Wang, et al., "Electrochemical study of dialcarb 'distillable' room-temperature ionic liquids", Chemphyschem, vol. 10, 2009, p. 455-461.*

Wei et al., "Research and Application of Ionic Liquids in Analytical Chemistry", Chinese Journal of Analytical Chemistry, Dec. 2007, pp. 1813-1819—English-language Abstract attached.

Xiaowei et al., "New Applications of Room Temperature Ionic Liquids", Specialty Petrochemicals, Mar. 2006, pp. 60-64—English-language Abstract attached.

Wei et al., "Applications of ionic liquids in electrochemical sensors", Analytica Chimica ACTA, 2008, pp. 126-135, vol. 607.

Buzzeo et al., "Use of Room Temperature Ionic Liquids in Gas Sensor Design", Analytical Chemistry, 2004, pp. 4583-4588, vol. 76, No. 15.

Buzzeo et al., "Non-Haloaluminate Room-Temperature Ionic Liquids in Electrochemistry—A Review", ChemPhysChem, 2004, pp. 1106-1120, vol. 5.

Silvester et al., "Electrochemistry in Room Temperature Ionic Liquids: A Review and Some Possible Applications", Z.Phys.Chem., 2006, pp. 1247-1274, vol. 220.

Earle et al., "Ionic liquids. Green solvents for the future", Pure Appl. Chem., 2000, pp. 1391-1398, vol. 72, No. 7.

Wasserscheid et al., "Ionic Liquids—New "Solutions" for Transition Metal Catalysis", Angew. Chem. Int. Ed., 2000, 38 pages, vol. 39.

Cai et al., "Studies on Sulfur Dioxide Electrochemical Sensor with Ionic Liquid as Electrolyte", Journal of East China Normal University (Natural Science), Sep. 2001, 11 pages, No. 3.

Haas et al., "Explosivstoff-Glossar" aus "Bestandsaufnahme von Rüstungsaltlastverdachtsstandorten in der Bundesrepublik Deutschland, Band 2", 1996, 18 pages.

* cited by examiner

US 8,623,189 B2

ELECTROCHEMICAL GAS SENSOR WITH AN IONIC LIQUID ELECTROLYTE SYSTEM INCLUDING AT LEAST ONE MONOALKYLAMMONIUM, DIALKYLAMMONIUM, OR TRIALKYLAMMONIUM CATION

CROSS-REFERENCE TO RELATED APPLICATIONS

This application claims the benefit of German Patent Application No. 10 2008 044 240.2, filed Dec. 1, 2008, the disclosure of which is incorporated herein by reference.

BACKGROUND

The basic measuring component of a gas sensor is an electrochemical cell, which includes at least two electrodes in contact with one another via an electrolyte (that is, an ionic conductor). On the side of the cell which is open to the atmosphere, gas can flow to one of the electrodes (the working or sensing electrode), at which it is electrochemically converted. The current generated by the conversion is proportional to the quantity of gas present. A signal, which can, for example, be used to provide an alarm, is generated from the current. A variety of electrolyte systems are described in the literature. Sulfuric acid is one of the most commonly used electrolytes, and is used in sensors for common gases, such as, for example, CO, $H_2S$, or $O_2$. See, for example, U.S. Pat. No. 3,328,277.

As some analyte gases are sufficiently reactive only in neutral electrochemical media, aqueous electrolytes including a neutral or a basic inorganic salt as a conducting salt have also been described. See, for example, U.S. Pat. No. 4,474,648 and German Patent No DE 4238337.

The electrolytes described therein are hygroscopic (that is, they can absorb water from the surround environment). A hydroscopic electrolyte can be desirable for use in dry or low-humidity environments to delay drying of the cell. In high-humidity environments, however, a hydroscopic electrolyte can absorb so much water that electrolyte leaks from the cell. To prevent this leakage of electrolyte, a sensor cell typically includes an extra or reserve volume of approximately five times to seven times its electrolyte filling volume. Inclusion of such a substantial reserve volume cuts against a general aim of reducing the overall size of sensor cells.

In a number of sensors, organic liquids, which include conducting salts admixed therein to ensure ionic conductivity, are used as electrolytes to limit water absorption in high-humidity environments. See, for example, U.S. Pat. No. 4,169,779. The advantage at high relative humidity, however, becomes a disadvantage at low humidity and/or high ambient temperatures, as vaporized solvent cannot be reabsorbed from the atmosphere and is thus irrecoverably lost from the sensor cell.

Ionic liquids (IL) have also been used as electrolytes. Ionic liquids are defined as liquid salts with a melting point below 100° C. The salt-like structure of certain ionic liquids results in the absence of a measurable vapor pressure. The properties of ionic liquids vary substantially and are dependent, for example, upon the type and the number of organic side chains present in the ionic liquid, as well as the anions and cations thereof. Ionic liquids are available having melting points below −40° C. Many ionic liquids are both chemically and electrochemically stable and exhibit high ionic conductivity. A number of ionic liquids are not measurably hygroscopic. Such properties make ionic liquids good electrolytes in electrochemical gas sensors.

The use of ionic liquids in gas sensors was first described for use in connection with high sulfur dioxide concentrations. Cai et al., Journal of East China Normal University (Natural Science), article number 1000-5641(2001)03-0057-04. The use of ionic liquids as electrolytes in gas sensors is also disclosed, for example, in Great Britain Patent No. GB 2395564, U.S. Pat. No. 7,060,169 and published German patent application DE 102005020719. GB 2395564 describes the use of ionic liquids as electrolytes generally. U.S. Pat. No. 7,060,169 discloses the use of pure imidazolium and pyridinium salts as ionic liquid electrolytes. Published German patent application DE 102005020719 discloses the possibility of forming an open gas sensor without a diffusion membrane. The potential for the use of such technology in miniaturizing sensors is described in published German patent application DE 102004037312.

Although ionic liquids are used in a number of gas sensors as a replacement for classic (aqueous) electrolytes, the chemical processes in ionic liquids differ fundamentally from those in aqueous and organic systems, and the chemical processes in ionic liquids are not well characterized. See, for example, P. Wasserscheid, Angew. Chem. 2000, 112, 3926-3945 and K. R. Seddon, Pure Appl. Chem. Vol. 72, No. 7, pp. 1391-1398, 2000.

SUMMARY

In one aspect, an electrochemical gas sensor includes an ionic liquid as electrolyte. The ionic liquid includes at least one cation selected from the group of a monoalkylammonium cation, a dialkylammonium cation, and a trialkylammonium cation. The individual alkyl groups of the cation can be branched or unbranched and can have 1 to 4 carbon atoms. The individual alkyl groups of the cation can be the same or different in case of the dialkylammonium cation and the trialkylammonium cation. In a number of embodiments, the individual alkyl groups have 2 to 4 carbon atoms.

The electrolyte of the electrochemical gas sensor can, for example, be absorbed to an extent of at least 90% in a solid material or the electrolyte can be present absorbent-free.

In a number of embodiments, the electrochemical gas sensor includes at least two electrodes, which are in ionic contact with the ionic liquid and which are electrically insulated from one another by at least one separator or by space.

Each electrode can for example, include (independently, the same or different) at least one metal from the group of Cu, Ni, Ti, Pt, Ir, Au, Pd, Ag, Ru, Rh, at least one oxide of a metal from the group of Cu, Ni, Ti, Pt, Ir, Au, Pd, Ag, Ru, Rh, a mixture of metals and/or metal oxides, or carbon.

In a number of embodiments, the at least one cation is ethylammonium.

The ionic liquid can, for example, include at least one anion from the group of a nitrate anion, a nitrite anion, a tetrafluoroborate anion, a hexafluorophosphates, a polyfluoroalkanesulfonate anion, a bis(trifluoromethylsulfonyl)imide anion, an alkyl sulfate anion, a alkanesulfonate anion, an acetate anion, and an anion of a fluoroalkanoic acid.

In several embodiments, the ionic liquid is ethylammonium nitrate.

In several embodiments, the electrolyte is absorbed in a powdered solid material which is a silicate having an average particle size of at least 5 µm, a specific surface area of at least 50 $m^2$/g, and a $SiO_2$ content of at least 95% by weight.

In several other embodiments, the electrolyte is absorbed in a fibrous nonwoven solid material, which is a glass fiber.

At least a part of the additive portion can, for example, be immobilized upon a solid support. At least a part of the additive portion can, for example, be immobilized upon the solid material. At least a part of the additive portion can, for example, be immobilized upon at least one of the electrodes.

The electrolyte can, for example, include an additive portion including at least one of an organic additive, an organometallic additive and an inorganic additive. The additive portion can, for example, be included in the electrolyte in a quantity of 0.05 to 15% by weight. An organic additive, when present, can, for example, be included in a quantity of 0.05 to 5.0% by weight. More particularly, an organic additive, when present, can, for example, be included in a quantity of 0.05 to 1.5% by weight. An inorganic additive, when present, can, for example, be included in a quantity of 1 to 12% by weight. An organometallic additive, when present, can, for example, be included in a quantity of 0.05 to 5.0% by weight. More particularly, an organometallic additive, when present, can, for example, be included in a quantity of 0.05 to 1% by weight.

In a number of embodiments, organic additives are, for example, be selected from the group of imidazole, a C1 to C4 alkyl imidazole, pyridine, a C1 to C4 alkyl pyridine, pyrrole, a C1 to C4 alkyl pyrrole, pyrazole, a C1 to C4 alkyl pyrazole, pyrimidine, a C1 to C4 alkyl pyrimidine, guanine, a C1 to C4 alkyl guanine, uric acid, benzoic acid, a porphyrine and a derivative of a porphyrine.

In a number of embodiments, organometallic additives are, for example, be selected from the group of metal phthalocyanines and derivatives thereof with $Mn^{2+}$, $Cu^{2+}$, $Fe^{2+/3+}$, or $Pb^{2+}$ as a the metal cation.

In a number of embodiments, inorganic additives are, for example, be selected from the group of an alkali halide, an ammonium halide, an ammonium halide substituted with at least one C1 to C4 alkyl group, a transition metal salt of $Mn^{2+}$, $Mn^{3+}$, $Cu^{2+}$, $Ag^+$, $Cr^{3+}$, $Cr^{6+}$, $Fe^{2+}$, or $Fe^{3+}$, and a lead salt of $Pb^{2+}$.

In a number of embodiments, the inorganic additive is selected from the group of lithium bromide, lithium iodide, ammonium iodide, tetramethylammonium iodide, tetraethylammonium iodide, tetrapropylammonium iodide, tetrabutylammonium iodide, tetrabutylammonium bromide, manganese(II)-chloride, manganese(II) sulfate, manganese(II) nitrate, chromium(III) chloride, alkali chromates, iron(II) chloride, iron(III) chloride, and lead(II) nitrate.

In another aspect, an electrochemical gas sensor as described above is used for the detection/measurement of an acid gas, a basic gas, a neutral gas, an oxidizing gas, a reducing gas, a halogen gas, halogen vapors, or a hydridic gas.

In still another aspect, an electrochemical gas sensor as described above is used for the detection/measurement of $F_2$, $Cl_2$, $Br_2$, $I_2$, $O_2$, $O_3$, $ClO_2$, $NH_3$, $SO_2$, $H_2S$, CO, $CO_2$, NO, $NO_2$, $H_2$, HCl, HBr, HF, HCN, $PH_3$, $AsH_3$, $B_2H_6$, $GeH_4$, or $SiH_4$.

The compositions, devices, systems, uses and/or methods hereof, along with the attributes and attendant advantages thereof, will best be appreciated and understood in view of the following detailed description taken in conjunction with the accompanying drawings.

DETAILED DESCRIPTION

Figure 1:
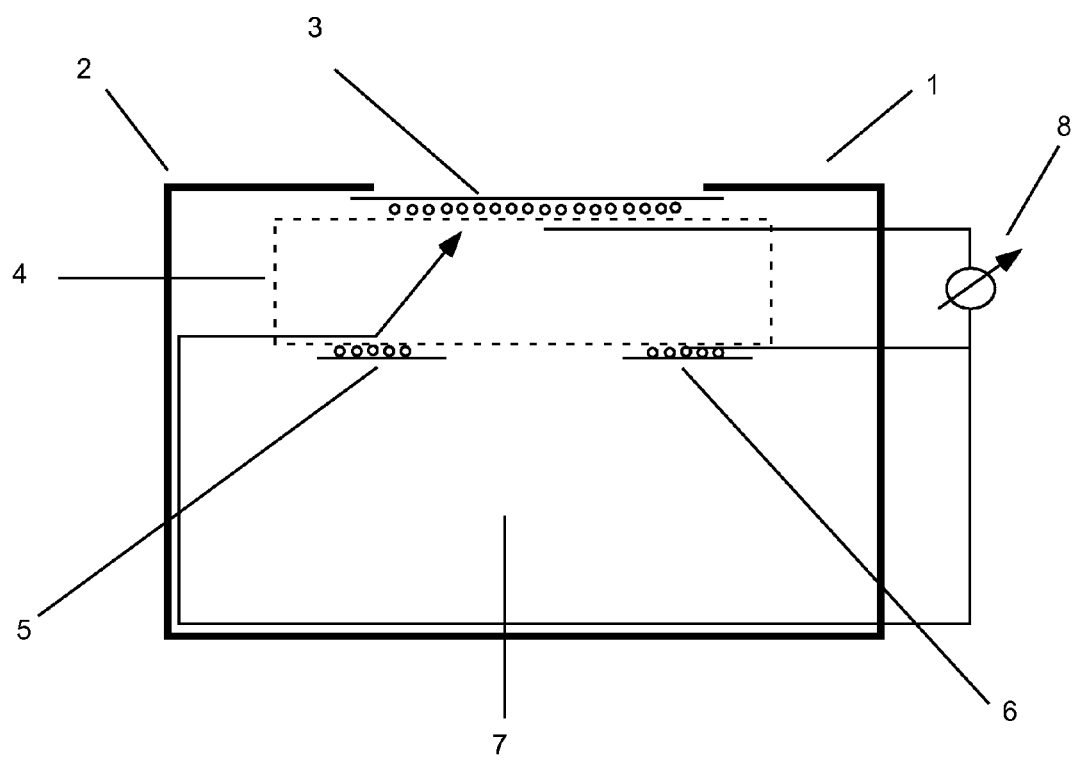
FIG. 1 illustrates a schematic representation of an embodiment of electrochemical gas sensor including three electrodes.

As used herein and in the appended claims, the singular forms "a," "an", and "the" include plural references unless the content clearly dictates otherwise. Thus, for example, reference to "an additive" includes a plurality of such additives and equivalents thereof known to those skilled in the art, and so forth, and reference to "the additive" is a reference to one or more such additives and equivalents thereof known to those skilled in the art, and so forth.

In certain sensors in which ionic liquids or mixtures thereof are used as electrolytes, the performance of the gas sensors with regard to sensitivity, response time, selectivity, and robustness suffers as compared to analogous sensors using classic (aqueous) electrolyte system. Furthermore, many ionic liquid electrolytes exhibit relatively high viscosities and tend to form gels, for example, if one attempts to incorporate one or more additives. For example, ionic liquids based on imidazole form gels when lithium salts are incorporated therein. Such gelling lowers the conductivity of the electrolyte and results in longer response times for the sensor.

In several representative embodiments of electrochemical gas sensor described herein, the sensor includes an ionic liquid as an electrolyte. The ionic liquid includes at least one cation selected from the group of a monoalkylammonium cation, a dialkylammonium cation, and a trialkylammonium cation. In several embodiments, the individual alkyl groups of the cation can be branched or unbranched and can have 1 to 4 carbon atoms. The individual alkyl groups of the cation are independently, the same or different, in case of a dialkylammonium cation and a trialkylammonium cation. In a number of embodiments, the individual alkyl groups have 2 to 4 carbon atoms. In several embodiments, the at least one cation is ethylammonium.

Although alkylammonium compounds are known as ionic liquids, a number of such compounds are also known to exhibit properties undesirable in electrolytes. For example, alkylammonium compounds including lower alkyl groups, such as methylammonium nitrate, are known to be oxidizing substances. Methylammonium nitrate is used in combination with hydrocarbons as a military explosive. For example, dimethylammonium nitrate has been used as a substitute explosive for TNT. See, for example, R. Haas, J. Thieme, Bestandsaufnahme von Rüstungsalt-lastverdachtsstandorten in der Bundesrepublik Deutschland, Volume 2, Explosivstofflexikon, 2nd Expanded Edition, UBA Texts 26/96, German Federal Environmental Agency (UBA) Berlin 1996.

Surprisingly, when incorporated into an electrochemical sensor, monoalkylammonium, dialkylammonium, and trialkylammonium ionic liquids do not exhibit those negative properties. For example, methylammonium nitrate incorporated in a sensor as an electrolyte does not react with the components of the sensor (for example, with highly catalytic platinum black), and can be handled without danger. Moreover, it was surprising that the ionic liquids have good fluidity, and do not gel (or gel very little) even if additives are added thereto.

In several embodiments, the ionic liquid of the electrolyte includes at least one anion from the group of a nitrate anion, a nitrite anion, a tetrafluoroborate anion, a hexafluorophosphate anion, a polyfluoroalkanesulfonate anion, a bis(trifluoromethylsulfonyl)imide anion, an alkyl sulfate anion, an alkanesulfonate anion, an acetate anion, and an anion of a fluoroalkanoic acid (for example trifluoroacetate). In a number of embodiments, the ionic liquid is ethylammonium nitrate.

In several embodiments, the electrolyte includes a mixture of different ionic liquids. A mixture of different ionic liquids can, for example, be used to achieve different polarities in the electrolyte. Controlling or adjusting polarity can aid in dissolving certain additives, and can also be helpful in controlling hygroscopicity and water absorption by the electrolyte. The hygroscopicity of the electrolyte influences the three-phase boundary at the working electrode.

The electrochemical gas sensor includes at least two electrodes, which are in contact with the ionic liquid electrolyte and which are electrically isolated from one another (for example, by separators or by space). Two-electrode, three-electrode, and multi-electrode sensor systems can be formed. In a number of representative embodiments, two- or three-electrode systems are formed. In a two-electrode system, there is one working electrode (WE) and one counter electrode (CE). In case of a three-electrode system, there is also a reference electrode (RE). In a multi-electrode system, the sensor may include a protective electrode or more than one working electrode. The electrodes can, for example, include a metal selected from the group of Cu, Ni, Ti, Pt, Ir, Au, Pd, Ag, Ru, Rh, oxides of such metals, mixtures of such metals and/or metal oxides, or carbon. The materials of the individual electrodes can be the same or different. The electrodes can have any suitable shape. In a number of representative studies, the potential of the working electrode was maintained to be generally constant. However, the potential of the working electrode can also be varied.

The electrolytes are well suited for use in electrochemical gas sensors for gases such as $F_2$, $Cl_2$, $Br_2$, $I_2$, $O_2$, $O_3$, $ClO_2$, $NH_3$, $SO_2$, $H_2S$, CO, $CO_2$, NO, $NO_2$, $H_2$, HCl, HBr, HF, HCN, $PH_3$, $AsH_3$, $B_2H_6$, $GeH_4$, and $SiH_4$.

In a number of embodiments, the electrolyte or electrolyte system includes an additive portion including at least one of an organic additive (for example, an organic compound), an organometallic additive (for example, an organometallic compound) and/or an inorganic additive (for example, an inorganic compound). The additive(s) can, for example, improve the performance of the gas sensors with regard to sensitivity, response time, selectivity, and robustness.

In a number of embodiments, an additive or additives as described above is/are mixed with the ionic liquid electrolyte and can be at least partially solubilized therein and/or at least partially suspended therein. In other embodiments, the additives can be immobilized upon a solid support or otherwise incorporated in, or form a part of, a solid support and placed in contact with the ionic liquid electrolyte. As used herein, the term "immobilized" refers to entities that are attached to a separate solid support, as well as to entities that form a portion or all of a solid support.

An additive can, for example, be immobilized upon a solid support by reacting the additive or a precursor thereof (for example, to form a covalent bond or an ionic bond) with a solid support such that the additive or an active residue of the additive is immobilized upon or within the solid support. An additive or a precursor thereof can also be immobilized upon a support by absorption, adsorption, chelation, hydrogen bonding, entrapment and/or other techniques known for immobilization of chemical entities. The method of immobilization should leave the immobilized additive or additives available for interaction with, for example, the electrolyte, the analyte and/or other entities.

An immobilized additive can, for example, be placed in close proximity to a specific area (for example, an inlet of the sensor, the working electrode and/or other electrode) to improve the efficacy of the immobilized additive (for example, via interaction or reaction with the analyte gas or another entity). A plurality of solid supports can be used to immobilize an additive or additives. An additive or additive can be immobilized upon or within a porous matrix. In a number of embodiments, an additive or additives is/are immobilized upon a solid material within or upon which the electrolyte is absorbed as described herein. An additive or additives can also or alternatively be immobilized upon the working electrode and/or other electrode.

The additive portion (that is, the organic, organometallic and/or inorganic additive(s)) can, for example, be included in quantities of 0.05 to 15% by weight. In a number of embodiments, an organic additive or additives are included in a quantity of 0.05 to 5.0% by weight. More particularly, in a number of embodiments, an organic additive or additives are included in a quantity of 0.05 to 1.5% by weight. In a number of embodiments, an inorganic additive or additives are included in a quantity of 1 to 12% by weight. In a number of embodiments, an organometallic additive or additives are included in a quantity of 0.05 to 5.0% by weight. More particularly, in a number of embodiments, an organometallic additive or additives are included in a quantity of 0.05 to 1% by weight.

In several embodiments, the at least one organic additive is selected from the group of imidazole, pyridine, pyrrole, pyrazole, pyrimidine, guanine (each of which can be unsubstituted or substituted with at least one C1 to C4 alkyl group), uric acid, benzoic acid, a porphyrine and a derivative of a porphyrine. The effect of organic additives may be based on a stabilization of the reference potential and/or the pH. Such stabilization provides advantages with, for example, acid gas analytes.

In several embodiments, the at least one organometallic additive is selected from the group of metal phthalocyanines and derivatives thereof with $Mn^{2+}$, $Cu^{2+}$, $Fe^{2+/3+}$, or $Pb^{2+}$ as the metal cation. Upon addition of metal phthalocyanines, the selectivity of the sensors to certain gases such as, for example, carbon monoxide can be substantially increased. Increased selectivity has been demonstrated in semiconductor gas sensors upon doping with phthalocyanine derivatives, resulting in increased conductivity at the working electrode. In the present case, the increase in sensitivity of the sensors cannot be explained by an increase in conductivity since graphite (carbon) or noble metal electrodes are used, not oxidic semiconductors.

A known problem in the field of electrochemical gas sensors is the strong cross sensitivity of sensors including platinum electrodes to CO. Because hydrogen sensors include platinum electrodes in classical sensor technology, it is de facto impossible to measure hydrogen in the presence of carbon monoxide. The use of a metal phthalocyanine additive can aid in increasing the selectivity of a sensor by increasing the specific solubility of gases in the ionic liquid of the electrolyte.

In several embodiments, the at least one inorganic additive is selected from the group of an alkali halide, an ammonium halide, an ammonium halide substituted with at least one C1 to C4 alkyl group, a transition metal salt from the group of salts of $Mn^{2+}$, $Mn^{3+}$, $Cu^{2+}$, $Ag^+$, $Cr^{3+}$, $Cr^{6+}$, $Fe^{2+}$, $Fe^{3+}$, and a lead salt of $Pb^{2+}$.

In a number of embodiments, the at least one inorganic additive is selected from the group of lithium bromide, lithium iodide, ammonium iodide, tetramethylammonium iodide, tetraethylammonium iodide, tetrapropylammonium iodide, tetrabutylammonium iodide, tetrabutylammonium bromide, manganese(II)-chloride, manganese(II) sulfate, manganese(II) nitrate, chromium(III) chloride, alkali chromates, iron(II) chloride, iron(III) chloride, and lead(II) nitrate.

Adding an alkali halide and/or an ammonium halide, such as for example LiI or $NR_4I$ (wherein R is H, a methyl group, an ethyl group, a butyl group or mixtures thereof), in low percentages (for example, 0.05 to 15%) leads to a observable increase in the sensitivity of the sensors to halogen gases and vapors. Higher alkali halides can be oxidized, for example, by $Cl_2$ gas. The following sensor reaction is possible.

Partial Reaction of Analyte

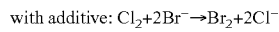

with additive: $Cl_2 + 2Br^- \rightarrow Br_2 + 2Cl^-$

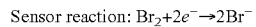

Sensor reaction: $Br_2 + 2e^- \rightarrow 2Br^-$

In this case, the reactions are secondary reactions of the salts in the electrolyte.

For $Cl_2$ sensors, addition of an additive to the ionic liquid electrolyte system results in greater sensitivity to the $Cl_2$ analyte gas as compared to sensors identical in construction, but including an ionic liquid electrolyte system without the additive(s).

Increasing sensitivity using additives such as inorganic additives provides the possibility to generate a specific test reaction for the target gas. By combining different additives, cross-sensitivity patterns can be generated that are not possible in classical (non-ionic liquid) sensor systems or with the use of pure ionic liquids as the electrolyte.

Mixtures of various additives can be used in the electrolyte. The additive mixture can be a mixture of additives of the same group (for example a mixture of different organic additives). The mixture of different additives can also include additives from different groups (for example, a mixture of organic and inorganic additives). Using mixtures of different additives, cross-sensitivity patterns of sensors can be adapted to specific requirements.

Additives can be added to the ionic liquids in the form of an aqueous solution, fused together with the ionic liquids, or suspended therein. The manner of addition depends on the water solubility of the additive, the hygroscopicity of the ionic liquid, and any expected secondary reaction.

Ionic liquids, either alone or including one or more additives from the group of organic compounds, organometallic compounds and/or inorganic compounds, function as ionic conductors in gas sensors in the classical sense of a Clark cell. The working electrode (WE) and counter electrode (CE) surfaces can, for example, include noble metal catalysts or carbon as described above for a two-electrode system. The electrolytes likewise function as ionic conductors in the case of a sensor including a reference electrode (RE) (that is, in three-electrode operation), or in the case that the sensor includes additional electrodes.

Two different embodiments of an electrochemical gas sensor were studied. In one embodiment, a quasi-solid electrolyte was used. In the case of embodiments of sensors including a quasi-sold electrolyte, the liquid electrolyte was absorbed in a powdered and/or fibrous nonwoven solid material (for example, $SiO_2$). In other embodiments, no absorbent was used. In such "absorbent-free" embodiments, the electrolyte is present, for example, in liquid, solid, or glass-like form.

The sensor can include a housing which includes at least one opening through which the gas to be detected enters the sensor. In another embodiment, electrodes can be imprinted upon a circuit board or upon flexible materials such as, for example, fabrics.

In quasi-solid electrolyte embodiments, the electrolyte is substantially absorbed in a solid material (for example, $SiO_2$) as described above. As used herein in connection with absorption of the electrolyte, the term "substantially" indicates that the ionic liquid is present and is absorbed to an extent of at least 90%. The electrolyte can also be absorbed to an extend of at least 95%, or even at least 99%. In several such embodiments, the electrochemical gas sensor included a housing with at least one inlet as described above. The at least two electrodes were arranged in the housing and were ionically interconnected via the electrolyte system, which included, for example, the quasi-solid electrolyte.

Position or orientation independence of the sensor performance is, among other things, important for an electrochemical gas sensor. Immobilizing liquid electrolytes using, for example, glass fibers or silicate structures to form a quasi-solid electrolyte improves position independence. With a quasi-solid electrolyte, reaction products and electrolytes are prevented from migrating through the sensor, and they cannot deposit on sensitive sites (for example, upon the working electrode or the reference electrode). Furthermore, there is no depletion as a result of leaching processes between the electrodes, which facilitates miniaturization of the sensor cells. Quasi-solid electrolyte systems are, for example, disclosed in U.S. Pat. Nos. 7,145,561, 7,147,761, 5,565,075 and 5,667,653. The systems described therein provide a good response time and allow for a compact design with the use conventional electrolytes.

The advantages of using a quasi-solid electrolyte with ionic liquid electrolytes is discussed in Published PCT International Patent Application WO 2008/110830 A1, which discloses an electrochemical sensor having an ionic liquid immobilized in a support material. A number of anions and cations are described for the ionic liquid. The cations disclosed include imidazolium, pyridinium, tetraalkylammonium, and tetraalkylphosphonium cations. The sensor is used for the detection of gases in the air exhaled by a patient to, for example, enable diagnosis of asthma. The sensor is operated in a cyclic voltammetric mode of operation. In cyclic voltammetry, the potential of the working electrode is varied between preset potential limits at a constant rate.

In several embodiments in which a quasi-solid electrolyte is used herein, the electrode materials are applied to a membrane permeable to gases or are directly mixed in the form of a powder with the electrolyte (that is, with the powdered solid material including the absorbed the ionic liquid). In the case that the electrode materials are directly applied to the quasi-solid electrolyte, care must be taken that electrolyte powder separates the electrode materials to prevent a short circuit between the electrodes.

The housing can be formed of metal or any other suitable material. Because ionic liquids, unlike conventional electrolytes such as sulfuric acid, are not highly corrosive, there are few if any problems with regard to corrosion of metallic housings. Polymers or plastics are also suitable as material for the housing.

In a number of representative embodiments, the powdered solid material used in forming the quasi-solid electrolyte is a silicate having an average particle size of at least 5 µm, at least 50 µm, or at least 75 µm; a specific surface area of at least 50 $m^2/g$, at least 100 $m^2/g$, or at least 150 $m^2/g$; and a $SiO_2$ content of at least 95% by weight. The term "silicate" includes variants of $SiO_2$ such as silica gels and silicates (for example, SIPERNAT® silica particles and SIDENT® silica, available from Evonik Degussa GMBH of Essen, Germany). In several embodiments, the silicate is pure $SiO_2$ or alumosilicates and calcium silicates. The specific surface area can vary widely. For example, a specific surface area in the range of 50 $m^2/g$ to 500 $m^2/g$ is suitable. In several embodiments, a silicate having an average particle size of 100 µm, a specific surface area of 190 $m^2/g$, and a $SiO_2$ content of at least 98% by weight is used.

In other embodiments of sensors including an absorbed electrolyte, the liquid electrolyte was absorbed upon a fibrous nonwoven solid material (for example, $SiO_2$) in the form of a glass fiber.

The solid material in which the liquid electrolyte is substantially absorbed can be present within the sensor as a bed, in a layered arrangement or in a compressed form. A bed or layered arrangement provides flexibility in the design of the sensors. Compression can take place in several steps. Compression to form as pellet provides advantages in production. The sensor can be assembled so that the pellet can be positioned between two electrodes. The entire assembly can be compressed by the sensor housing.

Electrodes can be compressed together with the compressed $SiO_2$ before being placed within the sensor to reduce assembly steps.

The ratio of electrolyte to the solid material (for example, $SiO_2$) can vary over a wide range. A ratio of electrolyte to solid $SiO_2$ material in the range of one to two parts to one to one part by weight is, for example, suitable. Even in the case of excess electrolyte, an almost dry powder is achieved (that is, the electrolyte is substantially absorbed to at least 90%, to at least 95%, and even to at least 99%). The resultant pellet can, for example, have a weight of approximately 200 mg, in which ½ to ⅔ of the weight is electrolyte and ½ to ⅓ of the weight is the solid material.

Sensor designs incorporating a quasi-solid electrolyte are disclosed in U.S. Pat. Nos. 7,145,561, 5,565,075, 7,147,761, and 5,667,653. The design and material of the housing as well as the arrangement and design of the quasi-solid electrolyte of those references can be adapted for use herein.

In all embodiments described above, the electrochemical gas sensors can be operated in different measuring modes such as, for example, an amperometric measuring mode. Analyte gases that can be sensed include acid gases, basic gases, neutral gases, oxidizing gases, reducing gases, halogen gases and vapors, and hydridic gases. The sensors can both qualitatively detect that an analyte gas is present and quantify the amount of gas present.

The sensors can, for example, be used for the detection and/or measurement of $F_2$, $Cl_2$, $Br_2$, $I_2$, $O_2$, $O_3$, $ClO_2$, $NH_3$, $SO_2$, $H_2S$, CO, $CO_2$, NO, $NO_2$, $H_2$, HCl, HBr, HF, HCN, $PH_3$, $AsH_3$, $B_2H_6$, $GeH_4$, or $SiH_4$.

FIG. 1 illustrates a representative gas sensor 1 including a sensor housing 2, in which a working electrode 3, a reference electrode 5, and a counter electrode 6 are positioned in such a way that working electrode 3 is in fluid connection with the ambient atmosphere via a gas permeable membrane. The electrodes are physically separated, but ionically interconnected via a separator 4 formed from glass fibers or silicate structures which are saturated with liquid electrolyte as described above. As described above, an additive or additives can be immobilized upon separator 4 or one or more other solid supports that can, for example, be positioned in the vicinity of the catalyst of working electrode 3a. An additive or additives can also or alternatively be immobilized upon working electrode 3a and/or upon another electrode. A compensating volume 7 provides volume for water to be absorbed in the case of a hygroscopic electrolyte. The sensor is connected to electronic measuring system 8, which can, for example, amplify the sensor current (resulting from the presence of analyte gas) to provide a measuring signal.

Figure 2:
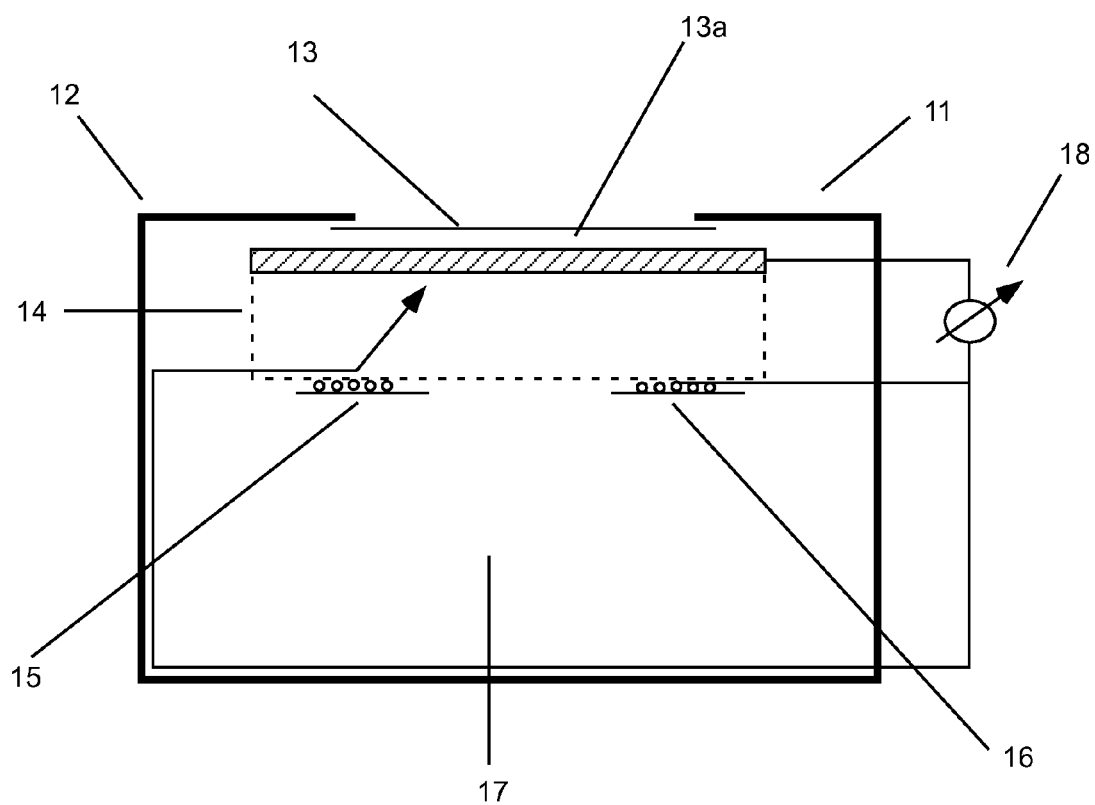
FIG. 2 illustrates a schematic representation of an embodiment of an electrochemical gas sensor including three electrodes and a quasi-solid electrolyte.

FIG. 2 illustrates another gas sensor 11 including a sensor housing 12. A working electrode 13a, a reference electrode 15, and a counter electrode 16 are positioned within housing 12 so that working electrode 13a is in fluid connection with the ambient atmosphere via a gas permeable membrane 13. Working electrode 13a includes a layer of catalyst/electrode material and electrolyte (that is, an ionic liquid, either with or without additive), which is absorbed in a powdered, solid $SiO_2$ material. The electrodes are physically separated but ionically interconnected via a separator 14 formed from glass fibers or silicate structures, which are saturated with electrolyte. Reference electrode 15 and counter electrode 16 are disposed side-by-side on the side of separator 14 opposite working electrode 13a. A compensating volume 17 provides volume for water to be absorbed in case of atmospheric variations of the humidity. Sensor 11 is connected to electronic measuring system 18, which can maintain a potential difference between working electrode 13a and reference electrode 15 and amplify the sensor current (resulting from the presence of analyte gas) to provide a measuring signal.

Figure 3:
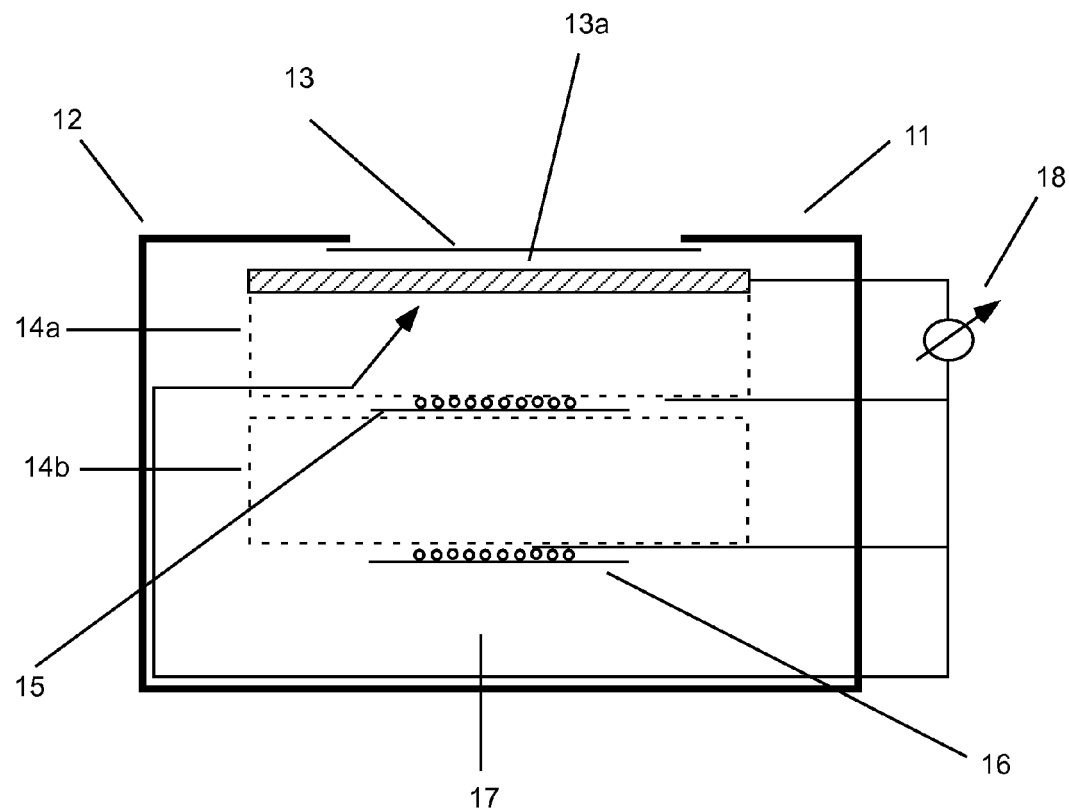
FIG. 3 illustrates a schematic representation of another embodiment of an electrochemical gas sensor including three electrodes and a quasi-solid electrolyte.

FIG. 3 illustrates another embodiment of a gas sensor 11 including a sensor housing 12 in which working electrode 13a, reference electrode 15, and counter electrode 16 are positioned so that working electrode 13a is in fluid connection with the ambient atmosphere via a gas permeable membrane 13. Working electrode 13a and reference electrode 15 are physically separated but ionically interconnected via a first separator 14a formed from glass fibers or silicate structures as described above. A second separator 14b is positioned between reference electrode 15 and counter electrode 16. Separators 14a and 14b include absorbed electrolyte as described above.

Figure 4:
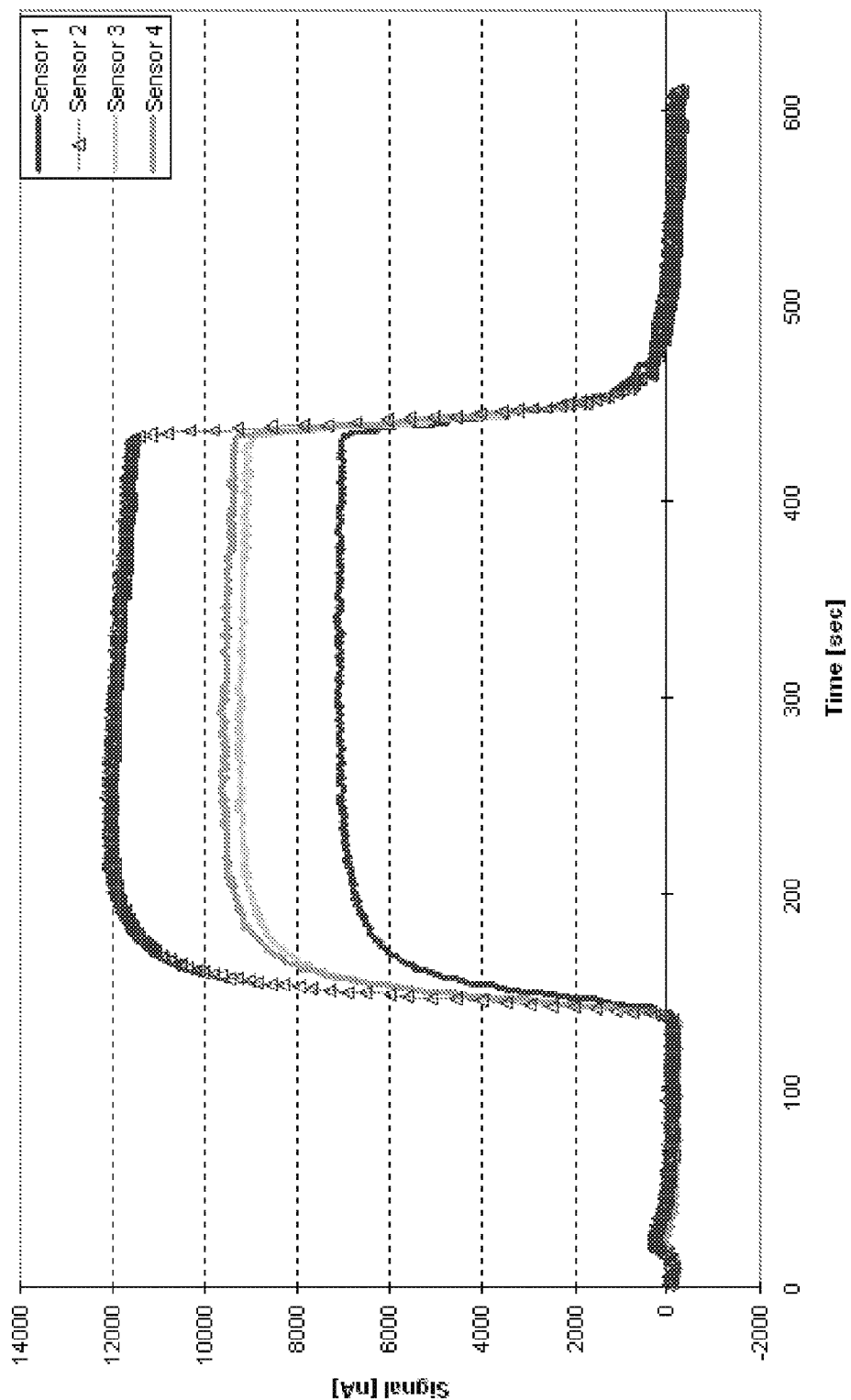
FIG. 4 illustrates a graph of sensor performance (signal as a function of time) for a family of four $NH_3$ sensors including ethylammonium nitrate as an electrolyte.

FIG. 4 illustrates the performance of a family of four $NH_3$ sensors (sensors 1-4) including ethylammonium nitrate as an electrolyte. Sensors 1-4 were exposed to 50 ppm of $NH_3$ in air.

Figure 5:
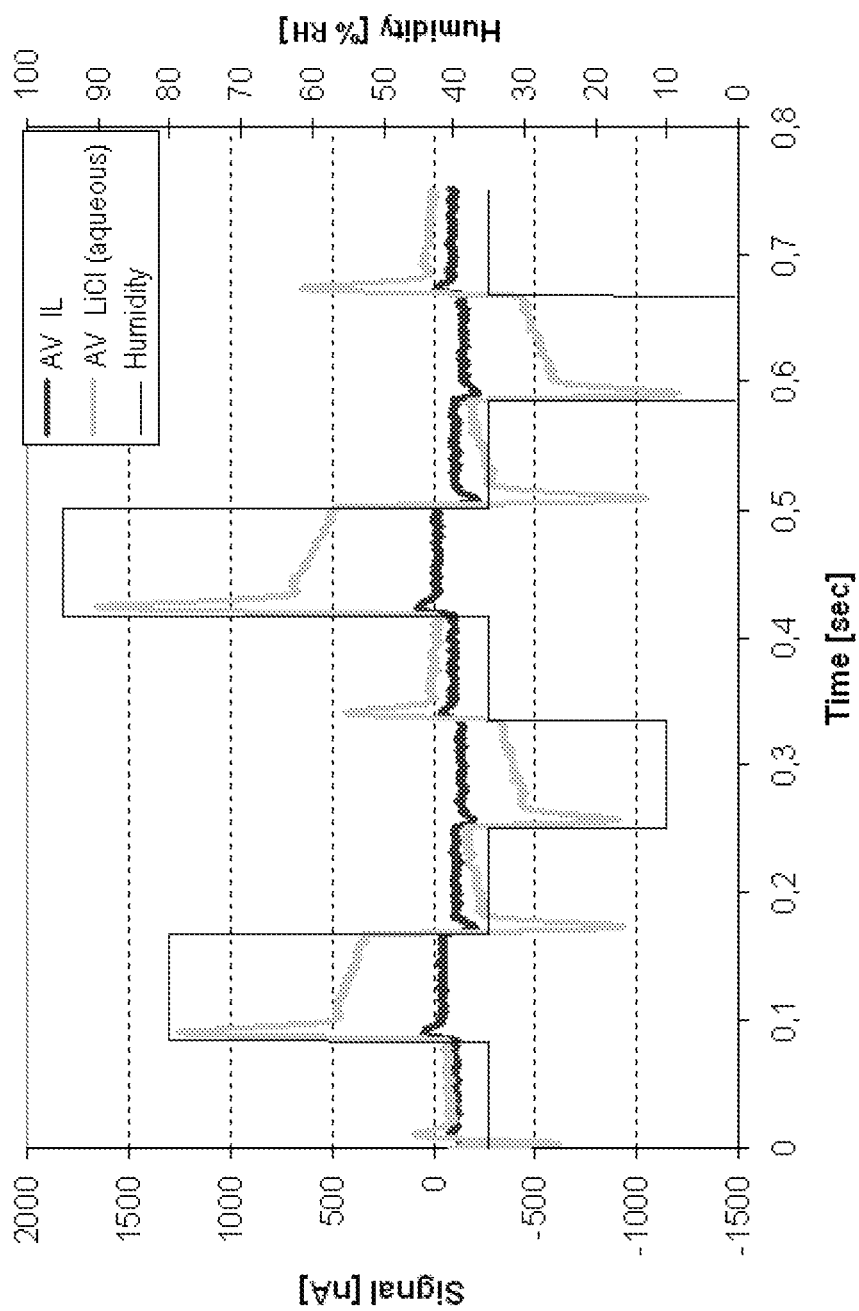
FIG. 5 illustrates a comparison of the humidity dependence of $NH_3$ sensors including ethylammonium nitrate as an electrolyte and $NH_3$ sensors including an aqueous lithium chloride solution (LiCl aqueous) as an electrolyte.

FIG. 5 illustrates a comparison of the humidity dependence of $NH_3$ sensors including ethylammonium nitrate as the electrolyte and $NH_3$ sensors including aqueous lithium chloride (LiCl aqueous) as the electrolyte in the absence of analyte gas (that is, under "zero current" conditions). With rapid changes in the ambient humidity, the sensors including the ionic liquid electrolyte exhibit a measurably lower response, while the sensors including the LiCl electrolyte system produce transients. Each of the curves in FIG. 5 set forth an average value (AV) of four sensors.

Figure 6:
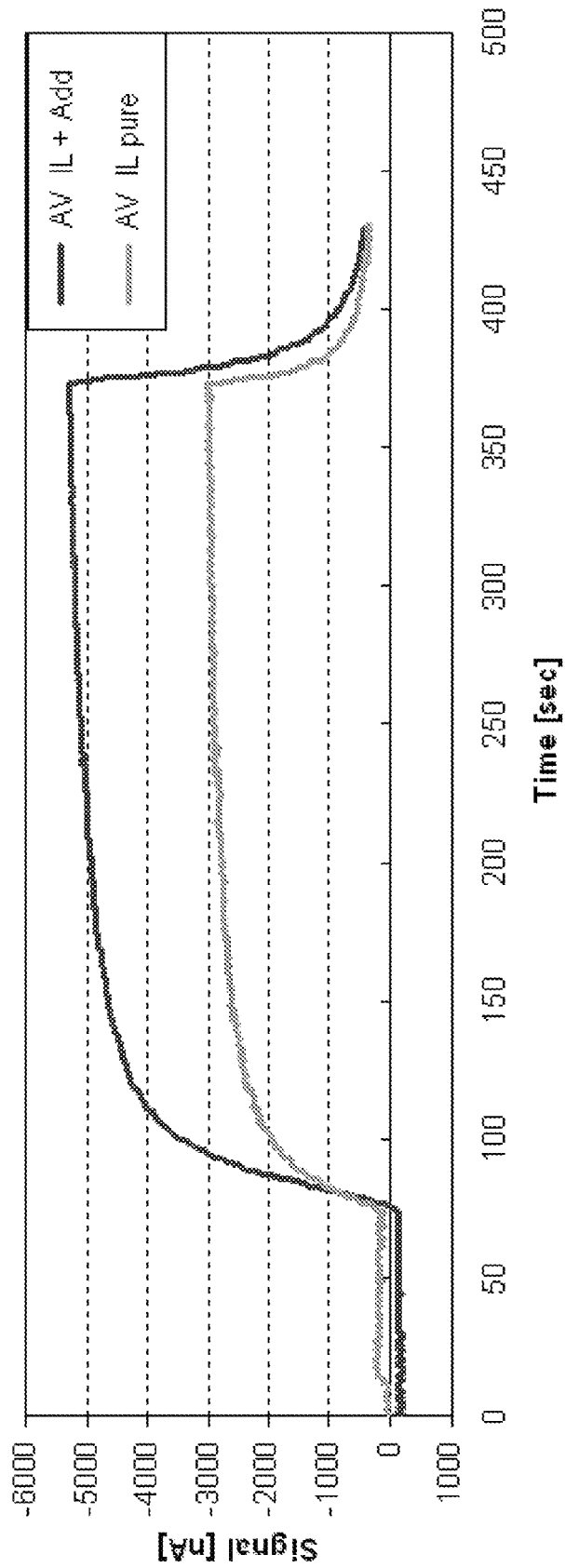
FIG. 6 illustrates a comparison of the performance (signal as a function of time) of $Cl_2$ sensors including pure ethylammonium nitrate as an electrolyte and $Cl_2$ sensors including ethylammonium nitrate and tetrabutylammonium iodide as an electrolyte.

FIG. 6 illustrates a comparison of performance of two groups of $Cl_2$ sensors (average values, AV, in each case), wherein one group of sensors included pure ethylammonium nitrate (IL pure) as the electrolyte and the other group of sensors included ethylammonium nitrate and tetrabutylammonium iodide (IL+Add) as the electrolyte. The performance is measurably improved in the sensors including the additive.

EXAMPLES

Example 1

$NH_3$ Sensor

The general design of the electrochemical sensor studied is set forth in the schematic illustration of FIG. 1. The working electrode (WE), counter electrode (CE), and reference electrode (RE), each included iridium. Each of the electrodes was applied to a gas permeable PTFE membrane. Separators saturated with electrolyte were positioned between the electrodes to provide ionic electrical conductivity between the electrodes and to prevent short circuits between the electrodes. The sensors also function if the RE and the CE are not arranged side by side, but at different longitudinal positions within the sensors (see FIG. 3). The electrolyte was ethylammonium nitrate ($EtNH_3NO_3$). The sensors were exposed to 50 ppm of $NH_3$ in air. Sensor signal (for four sensors) over time is represented graphically in FIG. 4.

Example 2

$NH_3$ Sensor

Comparison of Two $NH_3$ Sensors

The general design of the sensors was similar to that of Example 1. One group of sensors included an aqueous lithium chloride solution (LiCl aqueous) as the electrolyte, while the other group of sensors included ethylammonium nitrate (ionic liquid, IL) as the electrolyte. Both sensors were subjected to a rapid change of the ambient humidity. A significantly lower response (to changing humidity) of the sensor including the ionic liquid electrolyte was observed. The aqueous electrolyte system produced transients, which may trigger false alarms during use of the sensor. The results are represented graphically in FIG. 5. The curves represent average values (AV) of groups of four sensors.

Example 3

$Cl_2$ Sensor

The general design of the sensor was similar to that of Example 1. However, the WE, RE, and CE included a mixture of gold with carbon, which was applied to porous PTFE membranes. In one group of sensors, a pure ionic liquid (IL)—ethylammonium nitrate—was used as the electrolyte. The performance of that group of sensors was compared to a group of sensors having an electrolyte including ethylammonium nitrate with tetrabutylammonium iodide as an additive (IL+Add). Sensor performance was significantly improved upon including the additive. The results of the studies are represented graphically in FIG. 6.

The foregoing description and accompanying drawings set forth embodiments to the present time. Various modifications, additions and alternative designs will, of course, become apparent to those skilled in the art in light of the foregoing teachings without departing from the scope hereof, which is indicated by the following claims rather than by the foregoing description. All changes and variations that fall within the meaning and range of equivalency of the claims are to be embraced within their scope.

What is claimed is:

1. An electrochemical gas sensor comprising an ionic liquid electrolyte, wherein the ionic liquid comprises at least one cation selected from the group of a monoalkylammonium cation, a dialkylammonium cation, and a trialkylammonium cation, wherein the individual alkyl groups of the cation are branched or unbranched and have 1 to 4 carbon atoms, and wherein the individual alkyl groups of the cation are the same or different in case of the dialkylammonium cation and the trialkylammonium cation.

2. The electrochemical gas sensor according to claim 1, wherein the individual alkyl groups have 2 to 4 carbon atoms.

3. The electrochemical gas sensor according to claim 1, wherein the electrolyte of the electrochemical gas sensor is absorbed to an extent of at least 90% in a solid material or the electrolyte is present absorbent-free.

4. The electrochemical gas sensor according to claim 1, wherein the electrochemical gas sensor comprises at least two electrodes, which are in ionic contact with the ionic liquid and which are electrically insulated from one another by at least one separator or by space.

5. The electrochemical gas sensor according to claim 1, wherein each electrode comprises, independently, the same or different, at least one metal from the group of Cu, Ni, Ti, Pt, Ir, Au, Pd, Ag, Ru, Rh, at least one oxide of a metal from the group of Cu, Ni, Ti, Pt, Ir, Au, Pd, Ag, Ru, or Rh, mixtures thereof, or carbon.

6. The electrochemical gas sensor according to claim 1, wherein the at least one cation is ethylammonium.

7. The electrochemical gas sensor according to claim 1, wherein the ionic liquid comprises at least one anion from the group of a nitrate anion, a nitrite anion, a tetrafluoroborate anion, a hexafluorophosphates, a polyfluoroalkanesulfonate anion, a bis(trifluoromethylsulfonyl)imide anion, an alkyl sulfate anion, a alkanesulfonate anion, an acetate anion, and an anion of a fluoroalkanoic acid.

8. The electrochemical gas sensor according to claim 1, wherein the ionic liquid is ethylammonium nitrate.

9. The electrochemical gas sensor according to claim 1, wherein a powdered solid material in which the electrolyte is absorbed is a silicate having an average particle size of at least 5 μm, a specific surface area of at least 50 $m^2/g$, and a $SiO_2$ content of at least 95% by weight.

10. The electrochemical gas sensor according to claim 1, wherein a fibrous nonwoven solid material in which the electrolyte is absorbed is glass fiber.

11. The electrochemical gas sensor according to claim 1, wherein the electrolyte comprises an additive portion comprising at least one of an organic additive, an organometallic additive and an inorganic additive.

12. The electrochemical gas sensor according to claim 1, wherein the additive portion is included in the electrolyte in a quantity of 0.05 to 15% by weight.

13. The electrochemical gas sensor according to claim 1, wherein an organic additive, when present, is included in a quantity of 0.05 to 5.0% by weight, an inorganic additive, when present, is included in a quantity of 1 to 12% by weight, and an organometallic additive, when present, is included in a quantity of 0.05 to 5.0% by weight.

14. The electrochemical gas sensor according to claim 1, wherein the organic addition is selected from the group of imidazole, a C1 to C4 alkyl imidazole, pyridine, a C1 to C4 alkyl pyridine, pyrrole, a C1 to C4 alkyl pyrrole, pyrazole, a C1 to C4 alkyl pyrazole, pyrimidine, a C1 to C4 alkyl pyrimidine, guanine, a C1 to C4 alkyl guanine, uric acid, benzoic acid, a porphyrine and a derivative of a porphyrine.

15. The electrochemical gas sensor according to claim 1, wherein the organometallic additive is selected from the group of metal phthalocyanines and derivatives thereof with $Mn^{2+}$, $Cu^{2+}$, $Fe^{2+/3+}$, or $Pb^{2+}$ as the metal cation.

16. The electrochemical gas sensor according to claim 1, wherein the inorganic additive is selected from the group of an alkali halide, an ammonium halide, an ammonium halide substituted with at least one C1 to C4 alkyl group, a transition metal salt of $Mn^{2+}$, $Mn^{3+}$, $Cu^{2+}$, $Ag^+$, $Cr^{3+}$, $Cr^{6+}$, $Fe^{2+}$, or $Fe^{3+}$ and a lead salt of $Pb^{2+}$.

17. The electrochemical gas sensor according to claim 1, wherein the inorganic additive is selected from the group of lithium bromide, lithium iodide, ammonium iodide, tetramethylammonium iodide, tetraethylammonium iodide, tetrapropylammonium iodide, tetrabutylammonium iodide, tetrabutylammonium bromide, manganese(II) chloride, manganese(II) sulfate, manganese(II) nitrate, chromium (III) chloride, alkali chromates, iron(II) chloride, iron (III) chloride and lead(II) nitrate.

18. The electrochemical gas sensor according to claim 11, wherein at least a part of the additive portion is immobilized upon a solid support.

19. The electrochemical gas sensor according to claim 11, wherein at least a part of the additive portion is immobilized upon the solid material.

20. The electrochemical gas sensor according to claim 11, wherein at least a part of the additive portion is immobilized upon at least one of the electrodes.

* * * * *

UNITED STATES PATENT AND TRADEMARK OFFICE
CERTIFICATE OF CORRECTION

PATENT NO. : 8,623,189 B2  Page 1 of 1
APPLICATION NO. : 13/131391
DATED : January 7, 2014
INVENTOR(S) : Eckhardt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this
Twenty-second Day of September, 2015

Michelle K. Lee
*Director of the United States Patent and Trademark Office*